(12) United States Patent
Tsai et al.

(10) Patent No.: US 7,704,978 B2
(45) Date of Patent: *Apr. 27, 2010

(54) METHODS FOR TREATING NEUROPSYCHIATRIC DISORDERS

(75) Inventors: Guochuan Tsai, Cambridge, MA (US); Joseph Coyle, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 1135 days.

This patent is subject to a terminal disclaimer.

(21) Appl. No.: 11/175,832

(22) Filed: Jul. 5, 2005

(65) Prior Publication Data

US 2005/0250851 A1 Nov. 10, 2005

Related U.S. Application Data

(63) Continuation of application No. 10/668,583, filed on Sep. 23, 2003, now Pat. No. 6,974,821, which is a continuation of application No. 10/196,686, filed on Jul. 15, 2002, now Pat. No. 6,667,297, which is a continuation of application No. 09/834,351, filed on Apr. 13, 2001, now Pat. No. 6,420,351, which is a continuation of application No. 09/291,296, filed on Apr. 14, 1999, now Pat. No. 6,228,875.

(60) Provisional application No. 60/081,645, filed on Apr. 14, 1998.

(51) Int. Cl.
- A01N 57/00 (2006.01)
- A61K 31/42 (2006.01)
- A61K 31/195 (2006.01)

(52) U.S. Cl. .................... 514/119; 514/380; 514/561

(58) Field of Classification Search ................ 514/119, 514/380, 561

See application file for complete search history.

(56) References Cited

U.S. PATENT DOCUMENTS

| | | | |
|---|---|---|---|
| 3,873,722 A | 3/1975 | Smythies | |
| 5,015,740 A | 5/1991 | Kennis et al. | |
| 5,051,448 A | 9/1991 | Shashoua | |
| 5,061,721 A | 10/1991 | Cordi et al. | |
| 5,112,863 A | 5/1992 | Hashimoto et al. | |
| 5,168,103 A | 12/1992 | Kinney et al. | |
| 5,187,171 A | 2/1993 | Cordi | |
| 5,240,946 A | 8/1993 | Kinney et al. | |
| 5,260,324 A | 11/1993 | Cordi et al. | |
| 5,468,763 A | 11/1995 | Cordi et al. | |
| 5,482,967 A | 1/1996 | Natsugari et al. | |
| 5,633,281 A | 5/1997 | Teall et al. | |
| 5,837,730 A | 11/1998 | Javitt | |
| 5,854,286 A | 12/1998 | Javitt et al. | |
| 6,162,827 A | 12/2000 | Javitt | |
| 6,228,875 B1 * | 5/2001 | Tsai et al. ................... 514/380 |
| 6,355,681 B2 | 3/2002 | Javitt | |
| 6,361,957 B1 | 3/2002 | Javitt | |
| 6,420,351 B1 * | 7/2002 | Tsai et al. ................... 514/114 |
| 6,551,993 B1 | 4/2003 | Schneider | |
| 6,667,297 B2 * | 12/2003 | Tsai et al. ................... 514/119 |
| 6,974,821 B2 * | 12/2005 | Tsai et al. ................... 514/297 |
| 2002/0161048 A1 | 10/2002 | Javitt | |

FOREIGN PATENT DOCUMENTS

| | | |
|---|---|---|
| AU | 765603 | 9/2003 |
| DE | 41 17 629 A1 | 12/1992 |
| EP | 0 387 867 A1 | 9/1990 |
| EP | 0 432 039 A2 | 6/1991 |
| EP | 0 652 012 A1 | 5/1995 |
| EP | 0 696 586 A1 | 2/1996 |
| HU | P9200192 * | 7/1994 |
| HU | P9200192 A | 1/2003 |
| JP | 55 020747 A | 2/1980 |
| JP | H06-501454 | 2/1994 |
| JP | 08026986 A | 1/1996 |
| NZ | 508169 | 10/2003 |
| RU | 2096044 C1 | 11/1997 |
| RU | 2219924 | 12/2003 |
| WO | WO 89/05144 | 6/1989 |
| WO | WO 91/19493 | 12/1991 |
| WO | WO 97/20552 | 6/1997 |
| WO | WO 97/20553 | 6/1997 |
| WO | WO 97/45115 | 12/1997 |

OTHER PUBLICATIONS

Aharon-Peretz et al., "Neurobehavioral consequences of closed head injury in the elderly," *Brain Inj.* 11:871-5, 1997.

(Continued)

Primary Examiner—Raymond J Henley, III
(74) Attorney, Agent, or Firm—Fish & Richardson P.C.

(57) ABSTRACT

The invention provides methods for treating neuropsychiatric disorders such as schizophrenia, Alzheimer's Disease, autism, depression, benign forgetfulness, childhood learning disorders, closed head injury, and attention deficit disorder. The methods entail administering to a patient diagnosed as having a neuropsychiatric disorder a pharmaceutical composition containing (i) a therapeutically effective amount of D-alanine (or a modified form thereof), provided that the composition is substantially free of D-cycloserine, and/or (ii) D-serine (or a modified form thereof), and/or (iii) 105 to 500 mg of D-cycloserine (or a modified form thereof), and/or (iv) N-methylglycine (or a modified form thereof).

21 Claims, No Drawings

OTHER PUBLICATIONS

Barnes et al., "A Rating Scale for Drug-Induced Akathisia" *British Journal of Psychiatry* 154:672-676, 1989.

Bart et al., "Efficacy and Tolerance of D-Cycloserine in Drug-Free Schizophrenic Patients" *Biological Psychiatry* 40:1298-1300, 1996.

Baxter et al., "D-Cycloserine, a Novel Cognitive Enhancer, Improves Spatial Memory in Aged Rats" *Neurobiology of Aging* 15:207-213, 1994.

Baxter et al., "Modulation of the NMDA Receptor Complex by D-Cycloserine" *CNS Drug Reviews* 1:74-90, 1995.

Carlisimo et al., "Retrograde memory deficits in severe closed-head injury patients," *Cortex* 34:1-23, 1998.

Cascella et al., "d-Cycloserine adjuvant therapy to conventional neuroleptic treatment in schizophrenia: an open-label study" *Journal of Neural Transmission* 95:10-111, 1994.

Chessell et al., "D-Cycloserine, a putative cognitive enhancer, facilitates activation of the *N*-methyl-D-aspartate receptor-ionophore complex in Alzheimer brain" *Brain Research* 565:345-348, 1991.

Contreras, "D-Serine Antagonized Phencyclidine- and MK-801-Induced Stereotyped Behavior and Ataxia" *Neuropharmacology* 29:291-293, 1990.

Crane, "Cycloserine as an Antidepressant Agent" *The American Journal of Psychiatry* 115:1025-1026, 1959.

Cutler et al., "The Tolerability and Efficacy of Cycloserine in Alzheimer's Disease" *Am. Coll. Neuropsychopharmacol.* Annual Meeting, Puerto Rico, 1994.

D'Souza et al., "Glycine Site Agonists of the NMDA Receptor: A Review" *CNS Drug Reviews* 1:227-260, 1995.

Falk et al., "A Case Series of D-Cycloserine Added to Donepezil in the Treatment of Alzheimer's Disease" *J. Neuropsychiatry Clin. Neurosci.* 14:466-467, 2002.

Fishkin et al., "D-Cycloserine Attenuates Scopolamine-Induced Learning and Memory Deficits in Rats" *Behavioral and Neural Biology* 59:150-157, 1993.

Francis et al., "A Glycine Site as Therapeutic Target" Institute of Neurology, Miriam Marks Department of Neurochemistry; London, WC1N, 1PJ, United Kingdom, pp. 184-188.

Goff et al., "D-Cycloserine Added to Clozapine for Patients With Schizophrenia" *Am. J. Psychiatry* 153:1628-1630, 1996.

Goff et al., "Dose-Finding Trial of D-Cycloserine Added to Neuroleptics for Negative Symptoms in Schizophrenia" *Am. J. Psychiatry* 152:1213-1215, 1995.

Hashimoto et al., "D-Alanine inhibits methamphetamine-induced hyperactivity in rats" *European Journal of Pharmacology* 202:105-107, 1991.

Hinchliffe et al., "Towards a conceptualization of language and cognitive impairment in closed-head injury: use of clinical measures," *Brain Inj.* 12:109-32, 1998.

Javitt et al., "Glycyldodecylamide, a phencyclidine behavioral antagonist, blocks cortical glycine uptake: implications for schizophrenia and substance abuse" *Psychopharmacology* 129:96-98, 1997.

Javitt et al., "Reversal of Phencyclidine-Induced Hyperactivity by Glycine and the Glycine Update Inhibitor Glycyldodecylamide" *Neuropsychopharmacology* 17:202-204, 1997.

Kay et al., "The Positive and Negative Syndrome Scale (PANSS) for Schizophrenia" *Schizophrenia Bulletin National Institute of Mental Health* 13:261-276, 1987.

Kirkpatrick et al., "The Schedule for the Deficit Syndrome: An Instrument for Research in Schizophrenia" *Psychiatry Research* 30:119-123, 1989.

Kumashiro et al., "Free D-serine in post-mortem brains and spinal cords of individuals with and without neuropsychiatric diseases" *Brain Res.* 681:117-125, 1997.

Leiderman et al., "Preliminary Investigation of High-Dose Oral Glycine in Serum Levels and Negative Symptoms in Schizophrenia: An Open-Label Trial" *Biological Psychiatry*, 39:213-215, 1996.

Lindenmayer et al., "Five-Factor Model of Schizophrenia Initial Validation" t*The Journal of Nervous and Mental Disease* 182:631-638, 1994.

Lingjaerde et al., "The UKU side effects rating scale" *Scandinavian Society of Psychopharmacology Committee of Clinical Investigations (UKU)*; pp. 81-94, 1986.

Malhotra et al., "NMDA receptor function and human cognition the effects of ketamine in healthy volunteers" *Neuropsychopharmacology* 14:301-307, 1996.

Matsuoka et al., "D-Cycloserine, a Partial Agonist at the Glycine Site Coupled to N-Methyl-D-aspartate Receptors, Improves Visual Recognition Memory In Rhesus Monkeys" *The Journal of Pharmacology and Experimental Therapeutics* 278:891-897, 1996.

McKhann et al., "Clinical diagnosis of Alzheimer's disease: Report of the NINCDS-ADRDA Work Group under the auspices of Department . . . " *Neurology* 34:939-944, 1984.

Monahan et al., "Characterization of a [$^3$H]Glycine Recognition Site as a Modulatory Site of the *N*-Methyl-D-Aspartate Receptor Complex" *Journal of Neurochemistry* 53:370-375, 1989.

Morrison and Boyd, "Carboxylic Acids," Chapter 23, pp. 822-823, in *Organic Chemistry*, Fifth ed. Boston: Allyn and Bacon, Inc.

Nilsson et al., "Glycine and D-serine decrease MK-801-induced hyperactivity in mice" *J. Neural. Transm* 104:1195-1205, 1997.

Nishikawa et al., "PCP-induced abnormal behavior and c-fos gene expression in the brain as indices for neuroleptic-resistant symptoms of schizophrenia" *Folia Pharmacologica Japonica*, Patent Abstract XP-002117995, 1996.

Papp et al., "Antidepressant-like effects of 1-aminocyclopropanecarboxylic acid and D-cycloserine in an animal model of depression" *European Journal of Pharmacology* 316:145-151, 1996.

Prous et al., "D-Cycloserine" *Drugs of the Future* 19: 988-991, 1994.

Ramakers et al., "The Impaired Long-Term Potentiation in the CA1 Field of the Hippocampus of Cognitive Deficient Microencephalic Rats is Restored by D-Serine" *Neuroscience* 54:49-60, 1993.

Ramakrishna et al., "Betaine reverses toxic effects of aluminium: Implications in Alzheimer's disease (AD) and AD-like pathology" *Current Science* 75:1153-1156, 1998.

Randolph et al., "D-Cycloserine Treatment of Alzheimer Disease" *Alzheimer Disease and Associate Disorders* 8:198-205, 1994.

Riekkinen et al., "The Effects of D-Cycloserine on Cognition in Experimental Models of Alzheimer's Disease" *Neurology* 43:A292; Abstract XP-0021178979.

Rimland, "Dimethylglycine (DMG), a nontoxic metabolite, and autism"; *Editor's Notebook*; Abstract XP-002117993.

Rockstroh et al., "Effects of the Novel NMDA receptor antagonist SDZ EAA 494 on memory and attention in humans" *Psychopharmacology* 124:261-266, 1996.

Rosen et al., "A new rating scale for Alzheimer's Disease" *The American Journal of Psychiatry* 141:1356-1364, 1984.

Russell, "A Multiple scoring method for the assessment of complex memory functions" *Journal of Consulting and Clinical Psychology* 43:800-809, 1975.

Schuster et al., "D-Cycloserine reverse the working memory impairment of hippocampal-lesioned rats in a spatial learning task" *European Journal of Pharmacology* 224:97-98, 1992.

Simeon et al., "D-Cycloserine Therapy of Psychosis by Symptom Provocation" *Comprehensive Psychiatry* 11:80-88, 1970.

Simpson et al., "A Rating Scale for Extrapyramidal Side Effects" *Acta Psychiatr. Scand. Suppl.* 212:11-19, 1970.

Sirvio et al., "D-Cycloserine, a modulator of the *N*-methyl-D-aspartate receptor, improves spatial learning in rats treated with muscarinic antagonist" *Neuroscience Letters* 146:215-218, 1992.

Tanii et al., "Effects of Allosteric Agonists for NMDA Receptor and Their Derivatives on PCP-Induced Abnormal Behaviors in Rat" National Institute of Neuroscience, NCNP, Kodaira; XP-002117991; vol. 44, 1990.

Tanii et al., "Stereoselective Antagonism by Enantiomers of Alanine and Serine of Phencyclidine-Induced Hyperactivity, Stereotypy and Ataxia in the Rat" *The Journal of Pharmacology and Experimental Therapeutics* 269:1040-1048, 1994.

Tanii et al., "Stereoselective inhibition by D- and L-alanine of phencyclidine-induced locomotor stimulation in the rat" *Brain Research* 563:281-284, 1991.

Temple et al., "Chronic, post-injury administration of D-cycloserine, an NMDA partial agonist, enhances cognitive performance following experimental brain injury" Brain Research 741: 246-251, 1996.

Tsai et al., "A Preliminary Study of D-Cycloserine Treatment in Alzheimer's Disease" The Journal of Neuropsychiatry 10:224-226, 1998.

Tsai et al., "Improved cognition in Alzheimer's Disease with Short-Term D-Cycloserine Treatment" Am. J. Psychiatry 156:467-469, 1999.

Tsai et al., "Glycine Transporter I Inhibitor, N-Methylglycine (Sarcosine), Added to Antipsychotics for the Treatment of Schizophrenia" Biol. Psychiatry 55:452-456, 2004.

Vamvakides, "Nootropic activity of glycinergic derivatives in relation to their dualistic effects on cerebral monoamines" Boll. Chim. Farm. 133:369-373, 1994.

The Merck Index, 11th edition, 1989; entry for L-alanine (p. 199).

Office Action, in Patent No. 6,228,875, mailed May 25, 2000 (53 pages).

Fish & Richardson P.C., Reply to Office Action, in Patent No. 6,228,875, filed Nov. 22, 2000 (11 pages).

Office Action, in Patent No. 6,420,351, mailed Jun. 26, 2001 (19 pages).

Fish & Richardson P.C., Reply to Office Action, in Patent No. 6,420,351, filed Sep. 26, 2001 (7 pages).

Office Action, in Patent No. 6,667,297, mailed Oct. 8, 2002 (6 pages).

Fish & Richardson P.C., Reply to Office Action, in Patent No. 6,667,297, filed Apr. 8, 2003 (16 pages).

Office Action, in Patent No. 6,667,297, mailed Apr. 25, 2003 (17 pages).

Fish &Richardson P.C., Reply to Office Action, in Patent No. 6,667,297, filed Jun. 25, 2003 (34 pages).

Fish & Richardson P.C., Supplemental Reply to Office Action, in Patent No. 6,667,297, filed Jul. 15, 2003 (4 pages).

Notice of Allowance, in Patent No. 6,667,297, mailed Aug. 8, 2003 (6 pages).

Office Action, in Patent No. 6,974,821, mailed Mar. 25, 2004 (10 pages).

Fish & Richardson P.C., Reply to Office Action, in Patent No. 6,974,821, filed Jun. 25, 2004 (20 pages).

Office Action, in Patent No. 6,974,821, mailed Jul. 26, 2004 (7 pages).

Fish & Richardson P.C., Reply to Office Action, in Patent No. 6,974,821, filed Jan. 25, 2005 (8 pages).

Sughrue Mion, PLLC, Request for Reexamination, in Patent No. 6,228,875, filed Feb. 27, 2002 (30 pages).

Order Granting/Denying Request for Ex Parte Reexamination, in Patent No. 6,228,875, mailed May 17, 2002 (8 pages).

Office Action in Ex Parte Reexamination, in Patent No. 6,228,875, mailed Sep. 25, 2002 (9 pages).

Reexamination Interview Summary Form, in Patent No. 6,228,875, mailed Feb. 27, 2002 (1 page).

Draft Claim Amendment, in Patent No. 6,228,875, mailed Nov. 20, 2002 (14 pages).

Ex Parte Reexamination Interview Summary, in Patent No. 6,228,875 mailed Nov. 21, 2002 (3 pages).

Fish & Richardson P.C., Amendment and Response, in Patent No. 6,228,875, mailed Nov. 25, 2002 (34 pages).

U.S. Patent and Trademark Office, Decision Merging Reexamination Proceedings, in Patent No. 6,228,875, mailed Jul. 22, 2003 (2 pages).

Notice of Intent to Issue Ex Parte Reexamination Certificate, in Patent No. 6,228,875, mailed Feb. 23, 2004 (11 pages).

Sughrue Mion, PLLC, Second Request for Reexamination, in Patent No. 6,228,875 C1, mailed Feb. 5, 2003 (18 pages).

Order Granting/Denying Request for Ex Parte Reexamination, in Patent No. 6,228,875 C1, mailed Apr. 3, 2003 (6 pages).

Notice of Intent to Issue Ex Parte Reexamination Certificate, in Patent No. 6,228,875 C1, mailed Feb. 23, 2004 (11 pages).

van Berckel et al., "Efficacy and tolerance of D-cycloserine in drug-free schizophrenic patients" Biol. Psychiatry 40:1298-1300, 1996.

International Search Report, PCT/US99/08056, dated Oct. 21, 1999 (14 pages).

Hungarian Search Report, Application Serial No. P0101627, dated Jan. 27, 2003 (9 pages).

Gisabella et al., "Regulation of synaptic plasticity in a schizophrenia model," 102(37):13301-13306 (2005) (2 pages).

Goldberg, "Schizophrenia Insight from Rats," The Boston Globe, Sep. 5, 2005.

In re Recreative Technologies, 83 F3rd 1394, 38 USPQ $2^{nd}$ 1776 (Fed. Cir. 1996) (7 pages).

Kandel et al., Principles of Neural Science, $3^{rd}$ Edition, New York, NY: Elsevier Science Publication Co. pp. 863-867 (1991) (18 pages).

Lipska, "Neonatal disconnection of the rat hippocampus: a neurodevelopmental model of schizophrenia," Dialogues in Clinical in Neuroscience 4(4):361-367 (2002) (8 pages).

Nishikawa et al., "PCP-induced abnormal behaviour and c-fos gene expression in the brain as indices for neuroleptic-resistant symptoms of schizophrenia," Folia Pharmacologica Japonica 108(1):53-58 (1996) (6 pages).

Posey et al., "A pilot study of D-Cycloserine in subjects with autistic disorder," Am. J. Psychiatry 161:2115-2117 (2004) (3 pages).

Roche, brochure for "Diazepam" (Valium) (7 pages).

Silbernagl et al., "D-Serine is reabsorbed in rat renal pars recta," Am. J. Physiol. 276(6pt.2):F857-863 (1999) (7 pages).

Wada et al., "Effects of DN-2327, a new anxiolytic, diazepam and buspirone on exploratory activity of the rat in an elevated plus-maze," Psychopharmacology 104:444-450 (1991) (9 pages).

Davies Collison Cave, Notice of Entitlement, in Patent No. 765603, dated Jun. 7, 2002 (1 page).

Davies Collison Cave, Request to Amend a Complete Specification, in Patent No. 765603, dated Sep. 25, 2002 (6 pages).

Australian Examiner Arati Sardana, Grounds for Objection, in Patent No. 765603, dated Nov. 12, 2002 (1 page).

Davies Collison Cave, Response to Official Report, in Patent No. 765603, dated Jul. 3, 2002 (27 pages).

Australian Examiner Maria Lewis, Notice of Acceptance, in Patent No. 765603, dated Aug. 15, 2003 (2 pages).

Davies Collison Cave, Request to Amend a Complete Specification, in Patent No. 765603, dated Nov. 21, 2003 (4 pages).

Davies Collison Cave, Notice of References, in Patent No. 765603, dated Nov. 21, 2003 (2 pages).

Davies Collison Cave, Notice of References, in Patent No. 765603, dated Jan. 28, 2004 (2 pages).

Australian Commissioner of Patents Fatima Beattle, Standard Patent, in Patent No. 765603, dated Jan. 22, 2004 (31 pages).

Australian Patent Examiner Maria Lewis, Notice of Allowance, in Patent No. 765603, dated Jun. 25, 2004 (33 pages).

Smart & Biggar, Voluntary Submission of Information, in Patent No. 2328197, dated Apr. 28, 2004 (2 pages).

Smart & Biggar, Request for Special Order for Advance Examination, Voluntary Amendment and Voluntary Submission of Information, in Patent No. 2328197 (46 pages).

Canadian Intellectual Property Office, Office Action, in Patent No. 2328197, dated Dec. 19, 2005 (3 pages).

Smart & Biggar, Amendment/Remarks following Examiner's Report, in Patent No. 2328197, dated Jun. 16, 2006 (37 pages).

Canadian Intellectual Property Office, Office Action, in Patent No. 2328197, dated Aug. 2, 2006 (3 pages).

Smart & Biggar, Amendment/Remarks Following Examiner's Report, in Patent No. 2328197, dated Jan. 22, 2007 (14 pages).

Canadian Intellectual Property Office, Notice of Allowance, in Patent No. 2328197, dated Mar. 15, 2007 (2 pages).

Lloyd Wise, Tregear & Co., Replacement Claims, in Patent No. 1073432, dated Jan. 5, 2001 (6 pages).

European Patent Office, Office Action, in Patent No. 1073432, dated Aug. 27, 2002 (5 pages).

Lloyd Wise, Amended Claim Set, in Patent No. 1073432, dated Mar. 5, 2003 (17 pages).

European Patent Office, Office Action, in Patent No. 1073432, dated Oct. 23, 2003 (4 pages).

Lloyd Wise, Amended Claim Set, in Patent No. 1073432, dated (11 pages).

European Patent Office, Office Action, in Patent No. 1073432, dated Oct. 25, 2004 (6 pages).

Lloyd Wise, Request Interview, in Patent No. 1073432, dated Mar. 9, 2006 (11 pages).

European Patent Office, Summons, in Patent No. 1073432, dated Nov. 20, 2006 (4 pages).

Lloyd Wise, Response to Summons, in Patent No. 1073432, dated Jan. 16, 2007 (11 pages).

European Patent Office, Reply to Response to Summons, in Patent No. 1073432, dated Feb. 5, 2007 (2 pages).

Lloyd Wise, Oral Proceedings, in Patent No. 1073432, dated Feb. 8, 2007 (1 page).

European Patent Office, Communication under Rule 51(4) EPC, in Patent No. 1073432, dated Mar. 14, 2007 (28 pages).

Intellectual Property Office of New Zealand, Examination Report, in Patent No. 508160, dated Mar. 4, 2002 (2 pages).

J.D. Hardie & Co., Reply to Examination Report, in Patent No. 508160, dated Jun. 19, 2003 (11 pages).

Intellectual Property Office of New Zealand, Examination Report, in Patent No. 508160, dated Jul. 11, 2003 (1 page).

Intellectual Property Office of New Zealand, Examination Report, in Patent No. 508160, dated Sep. 30, 2003 (2 pages).

J.D. Hardie & Co., Reply to Examination Report, in Patent No. 508160, dated Oct. 16, 2003 (2 pages).

Intellectual Property Office of New Zealand, Examination Report, in Patent No. 508160, dated Nov. 10, 2003 (2 pages).

J.D. Hardie & Co., Reply to Examination Report, in Patent No. 508160, dated Nov. 27, 2003 (2 pages).

Russian Federation Patent Office, Official Action, in Patent No. 2219924, Jan. 2003 (4 pages).

Kolster Oy Ab, Response to Official Action, in Patent No. 2219924, dated Mar. 14, 2003 (15 pages).

Russian Federation Patent Office, Decision on Grant, in Patent No. 2219924, (8 pages).

Nabeshima T., "Future of anti-dementia agents," Sougourinshou 46(1):195-196 (1997) (translation enclosed).

Nishikawa et al., "Disturbed neurotransmission via the N-methyl-D-aspartate receptor and schizophrenia," Developments in Psychiatry (Biology of Schizophrenia) 10:197-207 (1994).

Takahisa and Imura, Merck Manual, Medical Book Services Ltd., 1995, $16^{th}$ ed, $3^{rd}$ print, p. 2008-2013 (translation enclosed).

Tanaka and Kato, New Pharmacology, Nankodo Co. Ltd., 1997, $3^{rd}$ ed, $2^{nd}$ print, p. 268-285, 306-311 (translation enclosed).

Ueda et al., "Decrease of mortality in mouse after head impact by the competitive N-Methyl-D-Aspartate (MNDA) receptor antagonists CGS 19755 and CGP 40116 - effectiveness, pharmacology and therapy of NMDA antagonists in head injury," Jpn. Pharmacol. Ther. 24(2):435-441 (1996) (translation enclosed).

European Patent Office, Extended Search Report in EP application No. 07075595.4, dated Jan. 12, 2010 (14 pages).

Japanese Patent Office, Notice of Reasons for Rejection in JP application No. 2000-543129, dated Nov. 12, 2009 (27 pages) (translation enclosed).

* cited by examiner

METHODS FOR TREATING NEUROPSYCHIATRIC DISORDERS

CROSS-REFERENCE TO RELATED APPLICATION

This application is a continuation of U.S. application Ser. No. 10/668,583, filed Sep. 23, 2003, now U.S. Pat. No. 6,974,821; which is a continuation of U.S. application Ser. No. 10/196,686, filed Jul. 15, 2002, now U.S. Pat. No. 6,667,297; which is a continuation of U.S. application Ser. No. 09/834,351, filed Apr. 13, 2001, now U.S. Pat. No. 6,420,351; which is a continuation of U.S. application Ser. No. 09/291,296, filed Apr. 14, 1999, now Reexamined U.S. Pat. No. 6,228,875; which claims the benefit of U.S. Provisional application Ser. No. 60/081,645, filed Apr. 14, 1998.

BACKGROUND OF THE INVENTION

Schizophrenia, Alzheimer's Disease, autism, depression, benign forgetfulness, childhood learning disorders, closed head injury, and attention deficit disorder are examples of neuropsychiatric disorders. Autism, for example, is a developmental mental disorder characterized by autistic behavior, social failure, and language delay. Alzheimer's Disease is a form of dementia that typically involves progressive mental deterioration, manifested by memory loss, confusion, and disorientation. Alzheimer's Disease typically is treated by acetylcholine esterase inhibitors such as tacrine hydrochloride or donepezil. Attention Deficit Disorder is a disorder that is most prevalent in children and is associated with increased motor activity and a decreased attention span. Attention Deficit Disorder commonly is treated by administration of psychostimulants such as Ritalin or Dexedrin. Depression is a clinical syndrome that includes a persistent sad mood or loss of interest in activities, which persists for at least two weeks in the absence of treatment. Conventional therapeutics include serotonin uptake inhibitors (e.g., PROZAC), monoamine oxidase inhibitors, and tricyclic antidepressants.

The term schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates.

Conventional antipsychotic drugs, which act on the dopamine $D_2$ receptor, can be used to treat the positive symptoms of schizophrenia, such as delusion and hallucination. In general, conventional antipsychotic drugs and the new atypical antipsychotic drugs, which act on the dopamine $D_2$ and $5HT_2$ serotonin receptor, are limited in their ability to treat cognitive deficits and negative symptoms such as affect blunting (i.e., lack of facial expressions), anergia, and social withdrawal.

SUMMARY OF THE INVENTION

The invention derives from the discovery that neuropsychiatric disorders characterized by a deficit in neurotransmission via the NMDA receptor can be alleviated by a compound that acts as an agonist of the glycine site on the NMDA receptor or an inhibitor of glycine uptake. The compound is either a partial agonist such as D-cycloserine, which can be used at a dosage of 105-500 mg, or a full agonist (e.g., D-serine or D-alanine) that is selective for the NMDA receptor (compared to the inhibitory glycine receptor and other receptors), or a glycine uptake inhibitor (e.g., N-methylglycine). The invention therefore provides new methods for treating neuropsychiatric disorders in patients (i.e., humans). Examples of disorders that can be treated by the methods of the invention include schizophrenia, Alzheimer's Disease, autism, depression, benign forgetfulness, childhood learning disorders, closed head injury, and attention deficit disorder. The methods entail administering to a patient diagnosed as suffering from such a neuropsychiatric disorder a pharmaceutical composition that contains a therapeutically effective amount of an agonist of the glycine site of the NMDA receptor or a glycine uptake inhibitor, which agonist is relatively selective for (a) the glycine site of the NMDA receptor, compared with (b) the inhibitory glycine receptor and other receptors. The pharmaceutical composition may include, for example, (i) a therapeutically effective amount of D-alanine (wherein the pharmaceutical composition is substantially free of D-cycloserine) and/or (ii) a therapeutically effective amount of D-serine, and/or (iii) D-cycloserine in an amount of 105-500 mg, and/or (iv) a therapeutically effective amount of N-methylglycine.

In variations of the methods described herein, D-serine, D-alanine, D-cycloserine, and/or N-methylglycine can be substituted with a salt, ester, or alkylated form of the amino acid, or a precursor of the amino acid that is converted (e.g., metabolized) into the amino acid in vivo (e.g., D-phosphoserine, L-phosphoserine, or L-phosphoserine, N,N,N-trimethylglycine (betaine), or N,N-dimethylglycine).

Typically, a dosage of 100 µg to 100 g (e.g., 1 mg to 100 g; 1 mg to 100 mg; 10 mg to 100 g; 10 mg to 10 g; or 10 to 500 mg) is suitable for D-alanine, D-serine, and N-methylglycine. D-cycloserine is administered at a dosage of 105 to 500 mg. When the patient is treated with both D-serine and D-alanine, D-serine and D-alanine can be administered to the patient simultaneously or sequentially, e.g., by formulating the D-serine and D-alanine as a single pharmaceutical composition or as two or more pharmaceutical compositions. Likewise, the patient can be treated with both D-serine and D-cycloserine, or D-serine and N-methylglycine, or D-alanine and N-methylglycine, or D-cycloserine and N-methylglycine simultaneously or sequentially. In one, but not the only, suitable method of treatment, the pharmaceutical composition is administered to the patient at least once daily for at least one week. If desired, the pharmaceutical composition can be administered to the patient in more than one dose per day (e.g., 2, 3, or 4 doses). Generally, the patient is treated for at least one week; typically, the patient is treated for at least several weeks (e.g., at least 4, 6, or 8 weeks) or months (e.g., at least 4, 8, or 12 months). If necessary, the treatment can continue indefinitely to keep the patient's symptoms under control throughout his or her life.

If desired, a pharmaceutical composition containing D-alanine (substantially free of D-cycloserine), D-serine, D-cycloserine and/or N-methylglycine (or a modified version thereof, as described herein) can be administered to a patient suffering from schizophrenia along with, or in sequence with, an art-known drug for treating schizophrenia (e.g., olanzapine, clozapine, haloperidol, and the like). Similarly, D-alanine (typically substantially free of D-cycloserine), D-serine, D-cycloserine and/or N-methylglycine (or a modified version thereof, as described herein) can be used in combination with, or in sequence with, other art-known antipsychotics (e.g., "typical," "atypical," and depot antipsychotics for treating schizophrenia and other psychotic conditions), antidepressants (for treating depression), psychostimulants (for treating attention deficit disorder, depression, or learning disorders), or Alzheimer's disease therapeutics (for treating Alzheimer's disease). Such pharmaceutical compositions are included within the invention. In general, the antipsychotic, antidepressant, psychostimulant, or Alzheimer's disease therapeutic typically is administered at a dosage of 0.25-5000 mg/d (e.g., 5-1000 mg/d). "Typical" antipsychotics are conventional antipsychotics such as phenothiazine, butyrophenones, thioxantheses, dibenzoxazepines, dihydroindolones, and diphenylbutylpiperidines. "Atypical" antipsychotics are a new generation of antipsychotics which generally act on the dopamine $D_2$ and $5HT_2$ serotonin receptor and have high levels of efficacy and a benign extrapyramidal symptom side effect profile. Examples of typical antipsychotics (and examples of suitable daily (d) dosages) include Chlorpromazine (5-2000 mg/d, e.g., 30-800 mg/d), Thioridazine (5-2000 mg/d, e.g., 20-800 mg/d), Mesoridazine (1-1000 mg/d, e.g., 30-400 mg/d), Fluphenazine (0.5-200 mg/d, e.g., 1-40 mg/d), Perphenazine (0.5-300 mg/d, e.g., 10-65 mg/d), Trifluoperazine (0.5-200 mg/d, e.g., 2-40 mg/d), Thiothixene (1-200 mg/d, e.g., 6-60 mg/d), Haloperidol (0.25-500 mg/d, e.g., 1-100 mg/d), Loxapine (1-1000 mg/d e.g., 20-250 mg/d), Molindone (1-1000 mg/d, e.g., 15-225 mg/d), Acetophenazine (10-2000 mg/d, e.g., 30-500 mg/d), Chlorprothixene (5-2000 mg/d, e.g., 30-500 mg/d), Droperidol (0.25-500 mg/d, e.g., 1-100 mg/d), Pimozide (0.25-500 mg/d, e.g., 1-100 mg/d). Examples of atypical antipsychotics (and examples of suitable daily dosages) include Clozapine (5-2000 mg/d, e.g., 12-900 mg/d), Risperidone (0.25-500 mg/d, e.g., 2-16 mg/d), Olanzapine (1-100 mg/d, e.g., 5-10 mg/d), and Quetiapine (1-2000 mg/d, e.g., 50-750 mg/d). Depot antipsychotics also can be used, e.g., Haloperidol decanoate (10-1000 mg/month, e.g., 100-450 mg/month), Fluphenazine decanoate (5-1000 mg/month, e.g., 25-150 mg/month), and Fluphenazine enanthate (5-1000 mg/month, e.g., 25-200 mg/month). Additional antipsychotics include Butaperazine (0.5-500 mg/d, e.g., 1-200 mg/d), Carphenazine, (0.5-3000 mg/d, e.g., 1-1000 mg/d), Remoxipride (0.5-5000 mg/d, e.g., 1-2000 mg/d), Piperacetazine (0.5-500 mg/d, e.g., 1-2000 mg/d), Sulpiride (0.5-5000 mg/d, e.g., 1-2000 mg/d), and Ziprasidone (0.5-500 mg/d, e.g., 1-200 mg/d). Examples of antidepressants that can be used include Amitriptyline (5-1000 mg/d, e.g., 50-300 mg/d), Amoxapine (5-1000 mg/d, e.g., 50-600 mg/d), Bupropion (5-1000 mg/d, e.g., 200-450 mg/d), Bupropion SR (5-1000 mg/d, e.g., 150-400 mg/d), Clomipramine (5-1000 mg/d, e.g., 25-250 mg/d), Desipramine (5-1000 mg/d, e.g., 100-300 mg/d), Doxepin (5-1000 mg/d, e.g., 75-300 mg/d), Fluoxetine (1-200 mg/d, e.g., 20-80 mg/d), Fluvoxamine (5-1000 mg/d, e.g., 50-300 mg/d), Imipramine (5-1000 mg/d, e.g., 75-300 mg/d), Maprotiline (5-1000, e.g., 75-225 mg/d), Mirtazapine (1-200 mg/d, e.g., 15-45 mg/d), Nefazodone (5-1000 mg/d, e.g., 200-600 mg/d), Nortriptyline (5-1000 mg/d, e.g., 75-150 mg/d), Paroxetine (1-200 mg/d, e.g., 10-60 mg/d), Phenelzine (1-500 mg/d, e.g., 5-90 mg/d), Protriptyline (1-200 mg/d, e.g., 15-60 mg/d), Sertraline (5-1000 mg/d, e.g., 50-200 mg/d), Tranylcypromine (1-200 mg/d, e.g., 30-60 mg/d), Trazodone (5-1000 mg/d, e.g., 150-600 mg/d), Trimipramine (5-1000 mg/d, e.g., 5-300 mg/d), Venlafaxine (5-1000 mg/d, e.g., 75-375 mg/d), and Venlafaxine XR (5-1000 mg/d, e.g, 75-225 mg/d). Psychostimulants that are particularly useful for treating attention deficit disorder include Dextroamphetamine (0.5-200 mg/d, e.g., 5-40 mg/d), Methamphetamine (0.5-200 mg/d, e.g., 5-25 mg/d), Methylphenidate (0.5-200 mg/d, e.g., 10-40 mg/d), and Pemoline (5-500 mg/d, e.g., 37.5-112.5 mg/d). Examples of Alzheimer's disease therapeutics that can be used in the invention include Donepezil (0.5-200 mg/d, e.g., 1-100 mg/d) and Tacrine (0.5-1000 mg/d, e.g., 10-500 mg/d). Thus, the invention also provides pharmaceutical compositions that contain D-alanine (typically substantially free of D-cycloserine), D-serine, D-cycloserine and/or N-methylglycine (or a modified version thereof, as described herein) along with an antipsychotic, antidepressant, psychostimulant, or Alzheimer's disease therapeutic.

If desired, one can measure negative and/or positive and/or cognitive symptom(s) of schizophrenia before and after treatment of the patient. A reduction in such a symptom indicates that the patient's condition has improved. Improvement in the symptoms of schizophrenia can be assessed using the Scales for the Assessment of Negative Symptoms (SANS) or Positive and Negative Syndrome Scale (PANSS) (see, e.g., Andreasen, 1983, *Scales for the Assessment of Negative Symptoms (SANS)*, Iowa City, Iowa and Kay et al., 1987, Schizophrenia Bulletin 13:261-276). Likewise, one can measure improvement of other neuropsychiatric disorders in patients who have been treated by the methods of the invention.

As used herein, the term "neuropsychiatric disorder" refers to a disease having a pathophysiological component of attenuated NMDA receptor-mediated neurotransmission. Examples of such disorders include schizophrenia, Alzheimer's disease, autism, depression, benign forgetfulness, childhood learning disorders, closed head injury, and attention deficit disorder.

As used herein, the term "schizophrenia" refers to a psychiatric disorder that includes at least two of the following: delusions, hallucinations, disorganized speech, grossly disorganized or catatonic behavior, or negative symptoms. Patients can be diagnosed as schizophrenic using the DSM-IV criteria (APA, 1994, *Diagnostic and Statistical Manual of Mental Disorders* (Fourth Edition), Washington, D.C.).

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease-and the Alzheimer's Disease and Related Disorders Association (NINCDS-ADRDA) criteria can be used to diagnose Alzheimer's Disease (McKhann et al., 1984, Neurology 34:939-944). The patient's cognitive function can be assessed by the Alzheimer's Disease Assessment Scale-cognitive subscale (ADAS-cog; Rosen et al., 1984, Am. J. Psychiatry 141: 1356-1364).

As used herein, the term "autism" refers to a state of mental introversion characterized by morbid self-absorption, social failure, language delay, and stereotyped behavior. Patients can be diagnosed as suffering from autism by using the DSM-IV criteria.

As used herein, the term "depression" refers to a clinical syndrome that includes a persistent sad mood or loss of interest in activities, which lasts for at least two weeks in the absence of treatment. The DSM-IV criteria can be used to diagnose patients as suffering from depression.

The term "benign forgetfulness," as used herein, refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale (Russell, 1975, J. Consult Clin. Psychol. 43:800-809).

As used herein, the term "childhood learning disorders" refers to an impaired ability to learn, as experienced by certain children. Such learning disorders can be diagnosed by using the DSM-IV criteria.

The term "closed head injury," as used herein, refers to a clinical condition after head injury or trauma which condition can be characterized by cognitive and memory impairment. Such a condition can be diagnosed as "amnestic disorder due to a general medical condition" according to DSM-IV.

The term "attention deficit disorder," as used herein, refers to a disorder that is most commonly exhibited by children and which can be characterized by increased motor activity and a decreased attention span. The DSM-IV criteria can be used to diagnose attention deficit disorder.

The terms "D-serine" and "D-alanine" refer to the D isomers of the amino acids serine and alanine, respectively. As D isomers, rather than L isomers, these amino acids are not naturally found in proteins.

"Negative" symptoms of schizophrenia include affect blunting, anergia, alogia and social withdrawal, which can be measured using SANS (the Scales for the Assessment of Negative Symptoms; see Andreasen, 1983, *Scales for the Assessment of Negative Symptoms* (*SANS*), Iowa City, Iowa).

"Positive" symptoms of schizophrenia include delusion and hallucination, which can be measured using PANSS (the Positive and Negative Syndrome Scale; see Kay et al., 1987, Schizophrenia Bulletin 13:261-276).

"Cognitive" symptoms of schizophrenia include impairment in obtaining, organizing, and using intellectual knowledge which can be measured by the Positive and Negative Syndrome Scale-cognitive subscale (PANSS-cognitive subscale)(Lindenmayer et al., 1994, J. Nerv. Ment. Dis. 182:631-638) or with cognitive tasks such as the Wisconsin Card Sorting Test.

A "full" agonist of the NMDA receptor is a compound that produces a maximal response at full receptor occupancy.

A "partial" agonist of the NMDA receptor is a compound that produces a lower maximal response at full receptor occupancy than do full agonists.

A "glycine uptake inhibitor of the NMDA receptor" is a compound that inhibits the re-uptake of glycine and increases the availability of glycine for the NMDA receptor (e.g., N-methylglycine).

The invention offers several advantages over many art-known methods for treating neuropsychiatric disorders. For example, unlike many conventional antipsychotic therapeutics, D-serine, D-alanine, and N-methylglycine can produce a desirable reduction in the positive, negative, and cognitive symptoms of schizophrenia. As shown by the examples set forth below, clinically significant improvement can be achieved even with patients who are poorly responsive to treatment by conventional antipsychotics. In addition, no significant side effects were detected after treatment of schizophrenia patients with D-serine, D-alanine, or N-methylglycine. In contrast, conventional antipsychotics typically lead to tardive dyskinesia (irreversible, involuntary movement disorder), extrapyramidal symptoms, and akathesia symptoms.

Other features and advantages of the invention will be apparent from the following detailed description, and from the claims.

DETAILED DESCRIPTION

The invention provides methods for treating a patient diagnosed as suffering from a neuropsychiatric disorder having a deficit in neurotransmission via the NMDA receptor (e.g., schizophrenia, Alzheimer's Disease, autism, depression, benign forgetfulness, childhood learning disorders, closed head injury, and attention deficit disorder). As described above, a variety of methods for diagnosing these disorders are known to those of skill in the art of clinical psychiatry, and any conventional diagnostic method can be used in conjunction with the invention.

The treatment method of the invention entails administering to a patient diagnosed as having a neuropsychiatric disorder a pharmaceutical composition containing a therapeutically effective amount of (i) an agonist of the glycine site of the NMDA receptor, which agonist is relatively selective for (a) the glycine site of the NMDA receptor, compared with (b) an inhibitory glycine receptor or any other receptor, or (ii) a glycine uptake inhibitor. For example, suitable pharmaceutical compositions may include (i) D-alanine substantially free of D-cycloserine and/or (ii) D-serine and/or (iii) N-methylglycine. D-serine and D-alanine are commercially available (e.g., from Spectrum Quality Products, Inc., Gardena, Calif.). Where D-alanine is used, the pharmaceutical composition is "substantially free" of D-cycloserine, meaning that the composition lacks D-cycloserine, or D-cycloserine is not included at a level sufficient to have a statistically significant effect upon the efficacy of the pharmaceutical composition, as determined by any method (e.g., by comparing PANSS and/or SANS scores before and after treatment of the patient). In general, this means that D-cycloserine is absent from the pharmaceutical composition or present in an amount such that the patient receives less than 0.02 mg/day.

Treatment includes administering a therapeutically effective amount of a composition containing D-alanine (substantially free of D-cycloserine) and/or D-serine and/or N-methylglycine to a patient in need of such treatment, thereby treating the neuropsychiatric disorder. Such compositions typically contain from about 0.1 to 90% by weight (such as 1 to 20% or 1 to 10%) of D-alanine, D-serine, or N-methylglycine in a pharmaceutically acceptable carrier. Regardless of the concentration of D-serine or D-alanine in the pharmaceutical composition, D-serine and/or D-alanine and/or N-methylglycine is administered to the patient at a dosage of 10 mg to 100 g. More typically, D-serine and/or D-alanine and/or N-methylglycine is administered at a dosage of 100 mg to 10 g. Generally, treatment continues for at least several weeks to several years or life-long as needed.

In an alternative method for treating a neuropsychiatric disorder in a patient, a pharmaceutical composition containing D-cycloserine in an amount equivalent to a dosage of 105 to 500 mg/day is administered to a patient in need of such treatment. For example, the dosage can be in an amount of 125 to 400 mg, such as 150 to 300 mg (e.g., 175 mg, 200 mg, 225 mg, or 250 mg). D-cycloserine (D-4-amino-3-isoxazolidinone) is commercially available from Eli Lilly, Inc. (Indianapolis, Ind.). Generally, treatment continues for at least one week and can continue for several years or life-long as needed to control the patient's symptoms.

In all of the methods of the invention, D-alanine, D-serine, and/or D-cycloserine and/or N-methylglycine can be substituted with a modified version of the amino acid, such as a salt, ester, alkylated form, or a precursor of the amino acid. For example, the amino acid can be in the form of a sodium salt, potassium salt, calcium salt, magnesium salt, zinc salt, or ammonium salt. Such salt forms of D-serine, D-alanine, N-methylglycine and D-cycloserine can be made in accordance with conventional methods (see, e.g., *Organic Chemistry*, pgs. 822-823, Morrison and Boyd, ed., Fifth Edition, Allyn and Bacon, Inc., Newton, Mass.). Other modified forms of D-serine, D-alanine, N-methylglycine and D-cycloserine also can be used in the methods of the invention. For example, the carboxy group of the amino acid can be converted to an ester group by reaction with an alcohol in accordance with standard esterification methods (Id. at 841-843). For example, alcohols having 1-20 carbon atoms can be used to produce an ester of D-serine, D-alanine, N-methylglycine or D-cycloserine for use in the invention (e.g., methyl-, ethyl-, propyl-, isopropyl-, butyl-, isobutyl-, sec-butyl-, tert-butyl-, pentyl-, isopentyl-, tert-pentyl-, hexyl-, heptyl-, octyl-, decyl-, dodecyl-, tetradecyl-, hexadecyl-, octadecyl-, and phenyl-alcohols can be used). In another variation, the amino group of the amino acid can be alkylated, using conventional methods, to produce a secondary or tertiary amino group by ammonolysis of halides or reductive amination (Id. at 939-948). For example, an alkyl group having 1-20 carbon atoms can be added to the amino acid to produce an alkylated amino acid (e.g., methyl-, ethyl-, propyl-, isopropyl-, butyl-, isobutyl-, sec-butyl-, tert-butyl-, pentyl-, isopentyl-, tert-pentyl-, hexyl-, heptyl-, octyl-, decyl-, dodecyl-, tetradecyl-, hexadecyl-, octadecyl- and phenyl-groups can be added to the amino acid). D-phosphoserine and L-phosphoserine are examples of precursors of D-serine, and are commercially available (e.g., from Sigma Chemical, St. Louis, Mo.). N,N,N-trimethylglycine (betaine) and N,N-dimethylglycine are examples of precursors of N-methylglycine.

In all of the methods of the invention, appropriate dosages of D-alanine, D-serine, D-cycloserine, or N-methylglycine (or modified versions thereof) can readily be determined by those of ordinary skill in the art of medicine by monitoring the patient for signs of disease amelioration or inhibition, and increasing or decreasing the dosage and/or frequency of treatment as desired.

The pharmaceutical compositions can be administered to the patient by any, or a combination, of several routes, such as oral, intravenous, trans-mucosal (e.g., nasal, vaginal, etc.), pulmonary, transdermal, ocular, buccal, sublingual, intraperitoneal, intrathecal, intramuscular, or long term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

EXAMPLES

The following examples demonstrate that D-alanine, D-serine, and N-methylglycine each can be used to treat a neuropsychiatric disorder in patients.

Patients

This study employed 37 patients who were diagnosed as having schizophrenia. All patients fulfilled the DSM-IV diagnosis of schizophrenia (APA, 1994, Diagnostic and Statistical Manual of Mental Disorders, Fourth Edition, Washington, D.C.). All of the patients also fulfilled the criteria of primary deficit syndrome, with a SANS score of more than 40 (Kirkpatrick et al., 1989, Psychiatry Research 30:119-123; Andreasen, 1983, Scales for the Assessment of Negative Symptoms (SANS), Iowa City, Iowa). All of the patients were poorly responsive to treatment by other antipsychotic drugs, and had been kept on a stable dose of an antipsychotic drug for at least 3 months prior to enrollment in this study.

Assessments

Several scales were used to assess the severity of the disorder in each patient. At the beginning of the study (i.e., the baseline), the PANSS, SANS, and Global Assessment Scales (CGI) were used. Each scale also was completed at the end of each 2-week period throughout the study. These assessments were performed by a psychiatrist who was blind to the treatment assignment. The Wisconsin Card Sort Test was used to provide a cognitive rating of the patients; in general, schizophrenic patients perform poorly on this test. The Wisconsin Card Sort Test was administered only at the initiation of the study and at the end of the 6-week study. To measure side effects, the Simpson-Angus Scale was used to measure extrapyramidal symptoms (EPS; Simpson et al., 1970, Acta Psychiatrica Scandinavia Suppl. 212:11-19). The Abnormal Involuntary Movement Scale (AIMS) was used to measure dyskinesia (Simpson et al., 1970, Acta Psychiatrica Scandinavia Suppl. 212:11-19). The Barnes Scale was used to measure akathesia (Barnes, 1989, Brit. J. Psychiatry 154:672-676). The side effects of D-serine, D-alanine, and N-methylglycine treatments were assessed biweekly according to the UKU side effects rating scale (*Scandinavian Society of Psychopharmacology Committee of Clinical Investigation: The UKU side effect rating scale: scale for the registration of unwanted effects of psychotropics*. Acta. Psychiatr. Scand. 1987; Suppl. 334:81-94).

Treatment and Results

Using double-blind conditions, the patients were randomly assigned to receive placebo (fruit juice), D-serine (30 mg/kg/day), D-alanine (60-100 mg/kg/day), or N-methylglycine (30 mg/kg/day) once a day by mouth for a period of 6 weeks. As indicated by the results shown in Table 1, treatment with D-serine, D-alanine, or N-methylglycine improved the schizophrenic symptoms and cognitive deficit of the patients. More specifically, treatment with D-serine resulted in a 21% reduction of the negative symptoms (on the SANS scale), and it resulted in a 17% reduction of the positive symptoms (on the PANSS-positive subscale). Treatment with D-alanine resulted in an 11% reduction of the negative symptoms and a 12% reduction of the positive symptoms. Treatment with N-methylglycine resulted in a 20% reduction of the negative symptoms and a 15% reduction of the positive symptoms. These reductions in the negative and positive symptoms represented clinically significant improvement. Treatment with each of D-serine, D-alanine, and N-methylglycine also improved cognition, as measured using the PANSS-cognitive subscale and the Wisconsin Card Sort Test. These results indicate that D-serine, D-alanine, and N-methylglycine are effective in treating schizophrenia even in patients who are poorly responsive to treatment by conventional antipsychotic drugs.

Using the UKU scale for rating side effects, no side effects were noted after treatment with D-serine, D-alanine, or N-methylglycine. In addition, there was no newly emergent tardive dyskinesia or worsening of extrapyramidal or akathesia symptoms. Thus, D-serine, D-alanine, and N-methylglycine offer an advantage over many conventional drugs for treating schizophrenia in that they do not cause significant side effects.

TABLE 1

Effects of D-serine, D-alanine, and N-methylglycine Treatment on Schizophrenia Patients

|  | D-serine | D-alanine | N-methyl-glycine | Placebo |
|---|---|---|---|---|
| Clinical Symptoms | | | | |
| Negative Symptoms | −21%* | −12%* | −20%* | −1% |
| Positive Symptoms | −17%* | −11%* | −15%* | 3% |
| CGI | 4.8->2.6* | 3.9->2.8* | 4.2->2.7* | 4.5->4.0 |
| Cognition | | | | |
| Cognitive symptoms | −12%* | −11%* | −12%* | 1% |
| WCST | +0.9 (category)* | +0.5* | +0.7* | −0.5 |
| Side Effects | | | | |
| EPS | 1.4-->1.7 | 3.1-->3.1 | 2.1-->2.1 | 3.3-->3.4 |
| AIMS | 0.3-->0.3 | 0.5-->0.1 | 0.4-->0.3 | 0.5-->0.9 |
| Barnes | 0.4-->0.8 | 0.4-->0.6 | 0.5-->0.6 | 0.9-->0.9 |

*Clinically significant improvement

OTHER EMBODIMENTS

It is to be understood that, while the invention has been described in conjunction with the detailed description thereof, the foregoing description is intended to illustrate and not limit the scope of the invention, which is defined by the appended claims. Other aspects, advantages, and modifications are within the scope of the following claims.

What is claimed is:

1. A method for treating a neuropsychiatric disorder in a patient, the method comprising administering to a patient suffering from a neuropsychiatric disorder a pharmaceutical composition comprising a therapeutically effective amount of a compound selected from the group consisting of N-methylglycine, a salt of N-methylglycine, an ester of N-methylglycine, alkylated N-methylglycine, and a precursor of N-methylglycine, wherein the pharmaceutical composition is administered at a dose equivalent to 10 mg to 10 g N-methylglycine per day.

2. The method of claim 1, wherein the neuropsychiatric disorder is schizophrenia.

3. The method of claim 1, wherein the compound is N-methylglycine.

4. The method of claim 1, wherein the compound is a salt of N-methylglycine selected from the group consisting of a sodium salt, a potassium salt, a calcium salt, a magnesium salt, a zinc salt, and an ammonium salt of N-methylglycine.

5. The method of claim 1, wherein the compound is an alkylated N-methylglycine having an alkyl group with 1-20 carbon atoms.

6. The method of claim 1, wherein the compound is a precursor of N-methylglycine, and the precursor is N,N,N-trimethylglycine or N,N-dimethylglycine.

7. The method of claim 1, further comprising administering to the patient at least one therapeutic agent selected from the group consisting of antipsychotics, antidepressants, psychostimulants, and Alzheimer's disease therapeutics.

8. The method of claim 7, wherein said therapeutic agent is selected from the group consisting of Chlorpromazine, Thioridazine, Mesoridazine, Fluphenazine, Perphenazine, Trifluoperazine, Thiothixene, Haloperidol, Loxapine, Molindone, Clozapine, Risperidone, Olanzapine, Quetiapine, Haloperidol decanoate, Fluphenazine decanoate, Fluphenazine enanthate, Amitriptyline, Amoxapine, Bupropion, Bupropion SR, Clomipramine, Desipramine, Doxepin, Fluoxetine, Fluvoxamine, Imipramine, Maprotiline, Mirtazapine, Nefazodone, Nortriptyline, Paroxetine, Phenelzine, Protriptyline, Sertraline, Tranylcypromine, Trazodone, Trimipramine, Venlafaxine, Venlafaxine XR, Dextroamphetamine, Methamphetamine, Methylphenidate, Pemoline, Donepezil, Tacrine, Acetophenazine, Chlorprothixene, Droperidol, Pimozide, Butaperazine, Carphenazine, Remoxipride, Piperacetazine, Sulpiride, and Ziprasidone.

9. The method of claim 8, wherein said therapeutic agent is Chlorpromazine or Risperidone.

10. The method of claim 1, wherein the pharmaceutical composition is administered for at least six weeks.

11. The method of claim 1, wherein the pharmaceutical composition is administered at a dose equivalent to 100 mg to 10 g N-methylglycine per day.

12. A method for treating a positive symptom of schizophrenia, the method comprising administering to a patient suffering from a positive symptom of schizophrenia a pharmaceutical composition comprising a therapeutically effective amount of a compound selected from the group consisting of N-methylglycine, a salt of N-methylglycine, an ester of N-methylglycine, alkylated N-methylglycine, and a precursor of N-methylglycine.

13. The method of claim 12, wherein the compound is N-methylglycine.

14. The method of claim 12, wherein the compound is a salt of N-methylglycine selected from the group consisting of a sodium salt, a potassium salt, a calcium salt, a magnesium salt, a zinc salt, and an ammonium salt of N-methylglycine.

15. The method of claim 12, wherein the compound is an alkylated N-methylglycine having an alkyl group with 1-20 carbon atoms.

16. The method of claim 12, wherein the compound is a precursor of N-methylglycine, and the precursor is N,N,N-trimethylglycine or N,N-dimethylglycine.

17. The method of claim 12, further comprising administering to the patient at least one therapeutic agent selected from the group consisting of antipsychotics, antidepressants, psychostimulants, and Alzheimer's disease therapeutics.

18. The method of claim 17, further comprising administering to the patient at least one therapeutic agent selected from the group consisting of Chlorpromazine, Thioridazine, Mesoridazine, Fluphenazine, Perphenazine, Trifluoperazine, Thiothixene, Haloperidol, Loxapine, Molindone, Clozapine, Risperidone, Olanzapine, Quetiapine, Haloperidol decanoate, Fluphenazine decanoate, Fluphenazine enanthate, Amitriptyline, Amoxapine, Bupropion, Bupropion SR, Clomipramine, Desipramine, Doxepin, Fluoxetine, Fluvoxamine, Imipramine, Maprotiline, Mirtazapine, Nefazodone, Nortriptyline, Paroxetine, Phenelzine, Protriptyline, Sertraline, Tranylcypromine, Trazodone, Trimipramine, Venlafaxine, Venlafaxine XR, Dextroamphetamine, Methamphetamine, Methylphenidate, Pemoline, Donepezil, Tacrine, Acetophenazine, Chlorprothixene, Droperidol, Pimozide, Butaperazine, Carphenazine, Remoxipride, Piperacetazine, Sulpiride, and Ziprasidone.

19. The method of claim 18, wherein the therapeutic agent is Chlorpromazine or Risperidone.

20. The method of claim 12, wherein the pharmaceutical composition is administered for at least six weeks.

21. A method for treating schizophrenia, the method comprising administering to a patient suffering from schizophrenia a pharmaceutical composition comprising a therapeutically effective amount of N,N,N-trimethylglycine or N,N-dimethylglycine.

* * * * *